United States Patent
Yanagihara

(10) Patent No.: US 9,289,901 B2
(45) Date of Patent: Mar. 22, 2016

(54) OPERATING MECHANISM OF MEDICAL DEVICE AND MEDICAL MANIPULATOR

(71) Applicant: OLYMPUS CORPORATION, Tokyo (JP)

(72) Inventor: Masaru Yanagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 25 days.

(21) Appl. No.: 14/157,635

(22) Filed: Jan. 17, 2014

(65) Prior Publication Data

US 2014/0135988 A1 May 15, 2014

Related U.S. Application Data

(63) Continuation of application No. PCT/JP2012/068901, filed on Jul. 19, 2012.

(30) Foreign Application Priority Data

Jul. 20, 2011 (JP) ................................. 2011-158835

(51) Int. Cl.
*G05B 15/00* (2006.01)
*B25J 9/16* (2006.01)
(Continued)

(52) U.S. Cl.
CPC ........... *B25J 9/1694* (2013.01); *A61B 19/2203* (2013.01); *B25J 13/04* (2013.01);
(Continued)

(58) Field of Classification Search
CPC combination set(s) only.
See application file for complete search history.

(56) References Cited

U.S. PATENT DOCUMENTS 5,784,542 A * 7/1998 Ohm .................. A61B 19/2203
700/247
5,994,864 A * 11/1999 Inoue ..................... B25J 9/1633
318/568.2

(Continued)

FOREIGN PATENT DOCUMENTS

EP 1 598 727 A1 11/2005
JP 02-071981 A 3/1990

(Continued)

OTHER PUBLICATIONS

Tanie, K. et al., A Study on the Torque Control of a DC Motor with Reduction Gears, Collection (Edition C) of Papers of Japan Society of Mechanical Engineers, (Jul. 1988) vol. 54, No. 503, pp. 1515-1519.

(Continued)

*Primary Examiner* — Jonathan L Sample
(74) *Attorney, Agent, or Firm* — Scully, Scott, Murphy & Presser, PC

(57) ABSTRACT

An operating mechanism of medical device includes a first shaft, a driving source which generates an auxiliary driving force, a second shaft which is operated by the auxiliary driving force, a connecting part which connects the first motion transmission part with the second motion transmission part, transmits the auxiliary driving force from the second motion transmission part to the first motion transmission part, wherein at least a part of the connecting part is capable of an elastic deformation; a detecting unit which detects at least one of a first operation amount of the first motion transmission part and a second operation amount of the second motion transmission part; a control unit that which controls the driving source based on the first operation amount and the second operation amount detected by the detecting unit; and a regulating unit which regulates so that an amount of the elastic deformation of the connecting part is equal to or more than a predetermined amount.

11 Claims, 18 Drawing Sheets

(51) Int. Cl.
*B25J 13/04* (2006.01)
*B25J 19/00* (2006.01)
*A61B 19/00* (2006.01)

(52) U.S. Cl.
CPC ..... *B25J 19/0004* (2013.01); *A61B 2019/2223* (2013.01); *A61B 2019/2269* (2013.01); *Y10S 901/09* (2013.01); *Y10T 74/20305* (2015.01)

(56) References Cited

U.S. PATENT DOCUMENTS

| | | | | |
|---|---|---|---|---|
| 8,924,021 | B2* | 12/2014 | Dariush | G06N 3/008 700/245 |
| 2003/0068607 | A1 | 4/2003 | Gregorio et al. | |
| 2003/0108415 | A1* | 6/2003 | Hosek | B25J 9/1664 414/783 |
| 2003/0220714 | A1* | 11/2003 | Nakamura | B25J 9/1633 700/245 |
| 2004/0167641 | A1* | 8/2004 | Kawai | A61B 5/1038 700/63 |
| 2006/0207419 | A1* | 9/2006 | Okazaki | B25J 9/142 91/35 |
| 2006/0250101 | A1* | 11/2006 | Khatib | B25J 9/1633 318/568.2 |
| 2007/0151389 | A1* | 7/2007 | Prisco | A61B 19/22 74/490.05 |
| 2007/0156122 | A1* | 7/2007 | Cooper | A61B 19/2203 606/1 |
| 2007/0200525 | A1* | 8/2007 | Kanaoka | G05D 1/0875 318/568.21 |
| 2007/0255454 | A1* | 11/2007 | Dariush | G06N 3/008 700/245 |
| 2008/0140257 | A1* | 6/2008 | Sato | B25J 9/1633 700/258 |
| 2009/0132088 | A1* | 5/2009 | Taitler | G05B 19/42 700/264 |
| 2009/0233720 | A1* | 9/2009 | Shim | B25J 17/0208 464/38 |
| 2009/0272585 | A1* | 11/2009 | Nagasaka | B25J 9/1633 180/8.6 |
| 2010/0030023 | A1* | 2/2010 | Yoshie | A61B 1/00147 600/117 |
| 2010/0032255 | A1* | 2/2010 | Conti | G05G 5/03 188/272 |
| 2010/0101342 | A1* | 4/2010 | Asai | B25J 17/00 74/89.2 |
| 2010/0152896 | A1* | 6/2010 | Komatsu | B25J 9/0003 700/258 |
| 2010/0152899 | A1* | 6/2010 | Chang | B25J 9/162 700/262 |
| 2010/0192720 | A1* | 8/2010 | Helmer | B25J 17/0266 74/490.06 |
| 2010/0326227 | A1* | 12/2010 | Choi | B25J 17/00 74/490.05 |
| 2010/0331820 | A1 | 12/2010 | Prisco et al. | |
| 2011/0060460 | A1* | 3/2011 | Oga | B25J 9/1633 700/254 |
| 2011/0067479 | A1* | 3/2011 | Davis | B25J 9/1692 73/1.75 |
| 2011/0067517 | A1 | 3/2011 | Ihrke et al. | |
| 2011/0071347 | A1* | 3/2011 | Rogers | A61B 1/00149 600/104 |
| 2011/0071543 | A1* | 3/2011 | Prisco | A61B 17/0218 606/130 |
| 2011/0160906 | A1* | 6/2011 | Orita | B62D 57/032 700/260 |
| 2011/0160907 | A1* | 6/2011 | Orita | B25J 9/1607 700/260 |
| 2011/0209570 | A1* | 9/2011 | Asai | F16H 25/18 74/25 |
| 2011/0218676 | A1* | 9/2011 | Okazaki | B25J 9/1075 700/260 |
| 2013/0000480 | A1* | 1/2013 | Komatsu | B25J 9/1615 92/48 |

FOREIGN PATENT DOCUMENTS

| | | |
|---|---|---|
| JP | 02-232188 A | 9/1990 |
| JP | 11-247882 A | 9/1999 |
| JP | 2006-084013 A | 3/2006 |
| JP | 2007-71336 A | 3/2007 |
| JP | 2007-225056 A | 9/2007 |
| JP | 2008055541 A | 3/2008 |
| JP | 2011083884 A | 4/2011 |

OTHER PUBLICATIONS

International Search Report dated Sep. 4, 2012 issued in PCT/JP2012/068901.
Japanese Office Action dated Jun. 2, 2015 in related Japanese Patent Application No. 2011-158835, together with English language translation.
Extended Supplementary European Search report dated Apr. 14, 2015 from related European Application No. 12 81 5448.1.

* cited by examiner

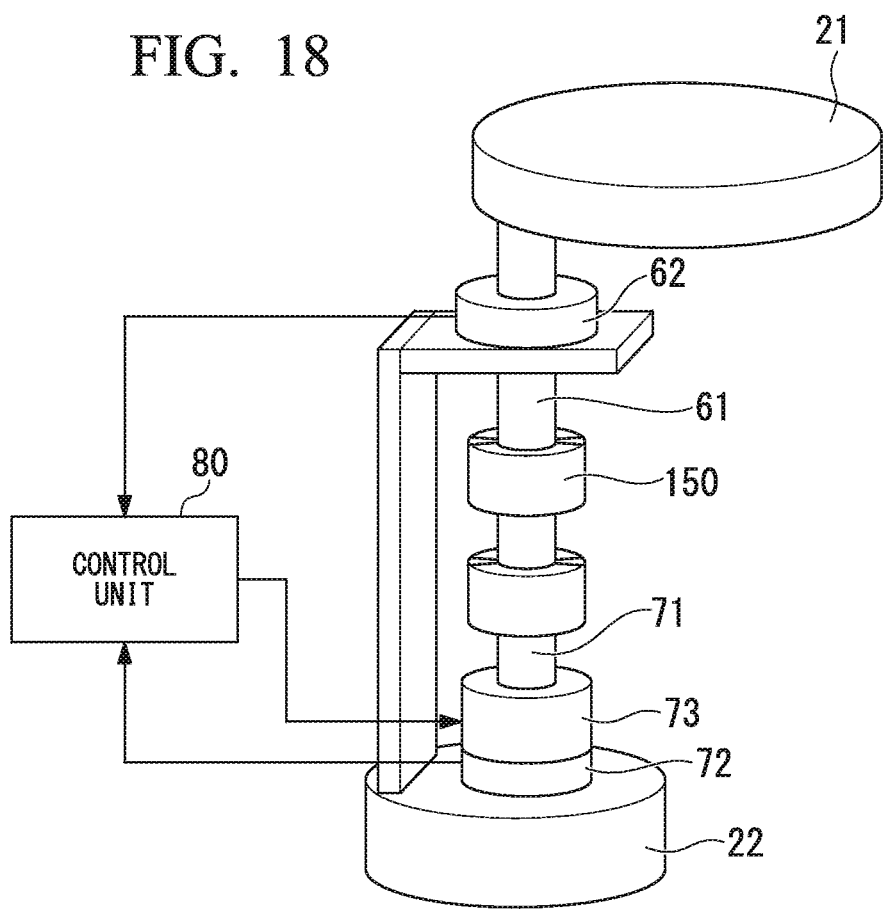

OPERATING MECHANISM OF MEDICAL DEVICE AND MEDICAL MANIPULATOR

This application is a continuation application based on PCT/JP2012/068901, filed on Jul. 19, 2012, claiming priority based on Japanese Patent Application No. 2011-158835, filed in Japan on Jul. 20, 2011. The contents of both the Japanese Patent Application and the PCT application are incorporated herein by reference.

BACKGROUND OF THE INVENTION

1. Field of the Invention

The present invention relates to an operating mechanism of medical device with an auxiliary driving force that assists a load-side manipulation input using a driving force, and a medical manipulator including the operating mechanism.

2. Description of Related Art

Conventionally, in manipulation devices of surgical robots, a manipulation arm with an auxiliary driving force is known. The manipulation arm is a member that assists manipulation of an operator with a driving force using a driving mechanism, such as a motor, and makes an operational feeling of an operator light, or the like, improving an operational feeling.

In the manipulation arm with an auxiliary driving force, torque is applied to the manipulation arm from the driving mechanism. However, if friction or backlash in the gears of the driving mechanism is transmitted to the operator, an operational feeling is deteriorated instead. Thus, controlling the torque applied to a load side, such as the manipulation arm, from the driving mechanism has been studied.

As an example, a mechanism that controls torque is described in Non-Patent Document 1 "A Study on the Torque Control of a DC Motor with Reduction Gears" by Kazuo Tanie et al, Collection (Edition C) of Papers of Japan Society of Mechanical Engineers, Volume 54, No. 503, pp 1515-9, Jul. 1988. In this mechanism, a torque sensor is installed at an output shaft, and torque control is performed by feeding back the output of the torque sensor to a motor current. However, a strain gauge torque sensor that is being used has problems with stability, noise tolerance, or the like when the torque sensor is a portion of the output shaft.

In order to solve the above problems, a mechanism that performs torque control using the detection of positional information only is described in Non-Patent Document 1 "A Study on the Torque Control of a DC Motor with Reduction Gears". In this mechanism, elastic bodies are inserted into the output shaft instead of the torque sensor, and an encoder, which detects the rotational angle of the output shaft on the motor side of the elastic bodies and the rotational angle of the output shaft on the load side, is provided. Then, torque control is performed by performing feedback based on the values of these rotational angles.

SUMMARY OF THE INVENTION

According to a first aspect of the invention, an operating mechanism of medical device includes a first motion transmission part fixed to a load-side member; a driving source configured to generate an auxiliary driving force that assists an operation of the first motion transmission part; a second motion transmission part configured to be operated by the auxiliary driving force; a connecting part which connects the first motion transmission part and the second motion transmission part, transmits the auxiliary driving force from the second motion transmission part to the first motion transmission part, wherein at least a part of the connecting part is capable of an elastic deformation; a detecting unit configured to detect at least one of the first operation amount of the first motion transmission part and the second operation amount of the second motion transmission part; a control unit configured to control the driving source based on the first operation amount and the second operation amount detected by the detecting unit; and a regulating unit configured to regulate so that an amount of the elastic deformation of the connecting part is equal to or more than a predetermined amount.

According to a second aspect of the invention, in the operating mechanism of medical device according to the first aspect, the regulating unit may be configured to limit the difference between the first operation amount of the first motion transmission part and the second operation amount of the second motion transmission part to less than a predetermined amount.

According to a third aspect of the invention, in the operating mechanism of medical device according to the second aspect, the regulating unit may be a mechanical stopper provided in a coupling position between the first motion transmission part and the second motion transmission part.

According to a fourth aspect of the invention, in the operating mechanism of medical device according to the third aspect, the stopper may have braking unit configured to brake at least one of the first motion transmission part and the second motion transmission part.

According to a fifth aspect of the invention, in the operating mechanism of medical device according to the second aspect, the operation detecting unit may have a first detector that detects the first operation amount of the first motion transmission part and a second detector that detects the second operation amount of the second motion transmission part, and the regulating unit may be configured to limit the difference to less than a predetermined amount based on the detection values of the first detector and the second detector.

According to a sixth aspect of the invention, the operating mechanism of medical device according to the fifth aspect may further include a determination unit that determines whether or not the regulating unit is made to operate based on the detection values of the first detector and the second detector.

According to a seventh aspect of the invention, in the operating mechanism of medical device according to the sixth aspect, the regulating unit may switch between an on-state and an off-state of transmission of the auxiliary driving force to the second motion transmission part from the driving source based on the determination of the determination unit.

According to an eighth aspect of the invention, in the operating mechanism of medical device according to the sixth aspect, the regulating unit may include braking unit configured to brake at least one of the first motion transmission part and the second motion transmission part based on the determination of the determination unit.

According to a ninth aspect of the invention, in the operating mechanism of medical device according to the sixth aspect, the control unit may control the operation of the driving source based on the determination of the determination unit, and function as the regulating unit.

According to a tenth aspect of the invention, in the operating mechanism of medical device according to the sixth aspect, the regulating unit may switch between an on-state and an off-state of transmission of an operating signal to the driving source from the control unit based on the determination of the determination unit.

According to an eleventh aspect of the invention, a medical manipulator may include the operating mechanism of medical device according to any one of the first to tenth aspects.

BRIEF DESCRIPTION OF THE DRAWINGS

FIG. 18 is a schematic perspective view showing the structure of a first joint section in a medical manipulator related to another modification of the embodiment of the invention.

DETAILED DESCRIPTION OF THE INVENTION

Figure 1:
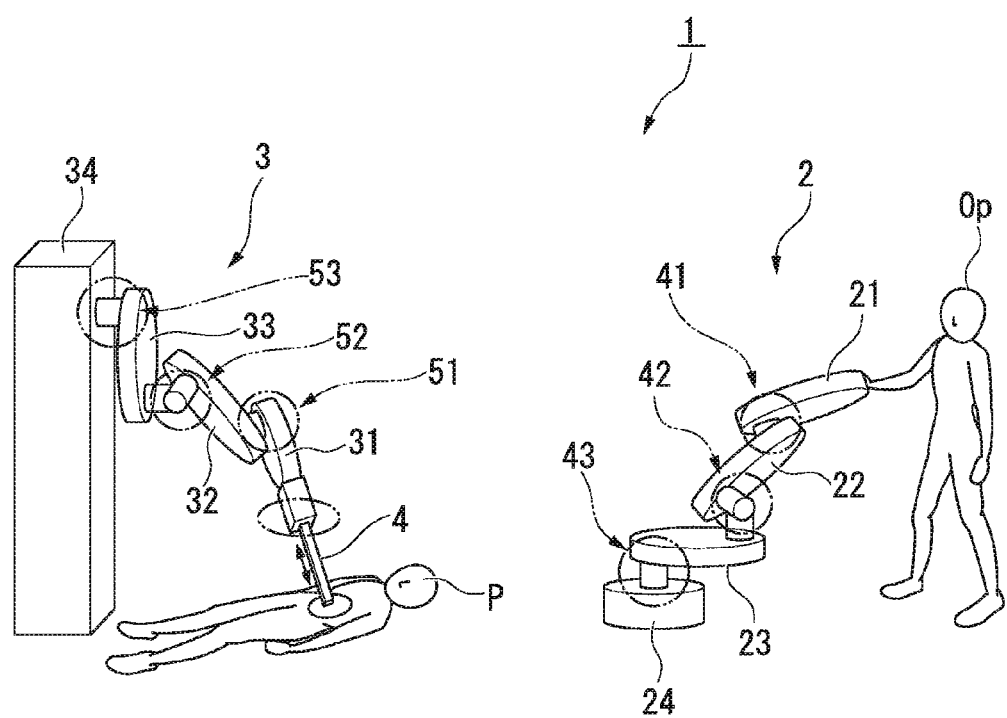
FIG. 1 is a view showing a medical manipulator to which an operating mechanism of medical device of a first embodiment of the invention is applied.

A first embodiment of the invention will be described below. FIG. 1 is a view showing the schematic configuration of a medical master and slave manipulator 1 to which an operating mechanism of the present embodiment is applied. The master and slave manipulator 1 includes a master arm 2 that is manipulated by an operator Op, and a slave arm 3 that operates in synchronization with the master arm 2. An operation tool 4 is attached to the distal end of the slave arm 3, and various procedures are performed on a patient P using this operation tool.

The master arm 2 has a first arm 21, a second arm 22, and a third arm 23. The first arm 21 and the second arm 22 are relatively rotatably connected by a first joint section 41, and the second arm 22 and the third arm 23 are relatively rotatably connected by a second joint section 42. The third arm 23 is relatively rotatably connected to a base 24 supporting the master arm 2 by a base joint section 43. The master arm 2 is configured so as to be able to perform multiaxial rotational operation as a whole.

The slave arm 3 has a number one arm 31, a number two arm 32, and a number three arm 33. The number one arm 31 and the number two arm 32 are relatively rotatably connected by a first joint section 51, and the number two arm 32 and the number three arm 33 are relatively rotatably connected by a second joint section 52. The number three arm 33 is relatively rotatably connected to a housing part 34 including a driving force transmission member or the like by the base joint section 53.

When the operator Op manipulates the master arm 2 and performs a medical action with the slave arm 3, the respective joint sections 51, 52, and 53 of the slave arm 3 receive manipulation signals, in which predetermined processing has been performed on a manipulation input to the master arm 2, and operate. As an example of a method of processing a manipulation input, angles that change the gear ratio scales using gears installed in the joint sections may be used as manipulation signals, and scales of motions between the master arm and the slave arm may be changed.

In the present embodiment, the respective numbers of arms of the master arm 2 and the slave arm 3 are three. In practice, however, the numbers of arms may be one or more, respectively, the numbers of arms of the master arm 2 and the slave arm 3 may not be the same, and the directions of rotation axes may be different.

Although all the respective joint sections 41, 42, and 43 of the master arm 2 include the operating mechanism of the embodiment of the invention, since the structures thereof are almost the same, the structure of the first joint section 41 will be described below in detail.

Figure 2:
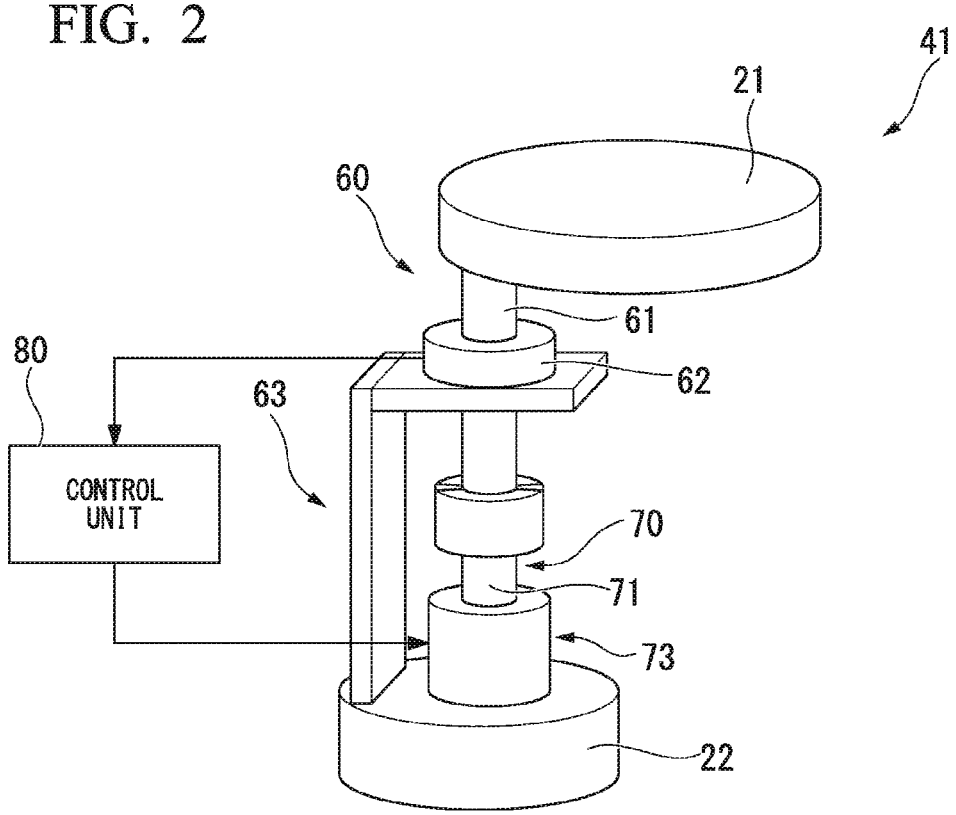
FIG. 2 is a schematic perspective view showing the structure of a first joint section of the medical manipulator of the first embodiment of the invention.

FIG. 2 is a schematic perspective view showing the structure of the first joint section 41. The first joint section (operating mechanism) 41 includes a first shaft part 60 fixed to the first arm 21 that is a load-side member, a second shaft part 70 that makes an auxiliary driving force act on the first shaft part 60, assisting load-side manipulation, and a control unit 80 that controls the assisting operation of the second shaft part 70.

The first shaft part 60 includes a first shaft (first motion transmission part) 61 and a first detector (detecting unit) 62 that detects the operation amount (first operation amount) of the first shaft 61. One end portion of the first shaft 61 is fixed to the first arm 21.

The second shaft part 70 includes a second shaft (second motion transmission part) 71, and a driving source 73 that rotates the second shaft 71 using an auxiliary driving force. One end portion of the second shaft 71 is rotatably supported by the second arm 22. Additionally, as the driving source 73, for example, a motor, or the like, capable of rotating normally and rotating reversely can be used, and a motor in which gears or the like are installed is also included.

In the present embodiment, a well-known rotary encoder or the like can be used as the first detector 62 because both the first shaft 61 and the second shaft 71 are rotated around an axis. The first detector 62 is attached in the vicinity of the first shaft 61 so as not to rotate together with the first shaft 61. Additionally, the first detector 62 is supported by a support 63 fixed to the second arm 22.

With respect to the first shaft 61 and the second shaft 71, the end portion of the first shaft 61 is coaxially (including substantially the same axis, hereafter the same) connected to the second shaft 71 so that an auxiliary driving force can be transmitted to the first shaft 61 from the second shaft 71.

Figure 3A:
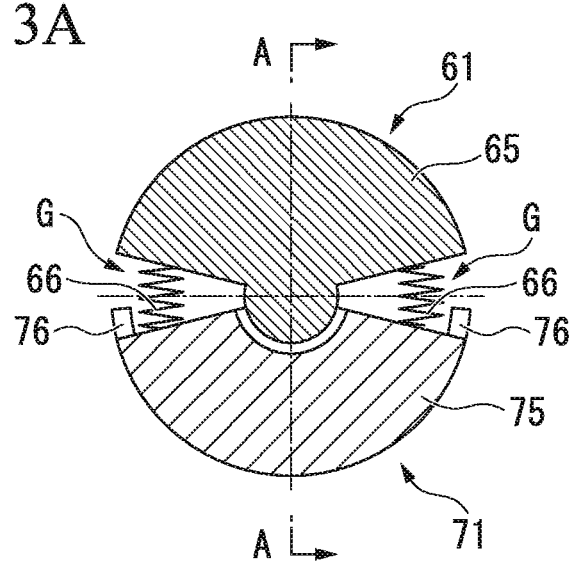
FIG. 3A is a cross-sectional view of a connecting portion between a first shaft and a second shaft of the first joint section of the medical manipulator of the first embodiment of the invention, in the direction orthogonal to the axis of the first shaft.
Figure 3B:
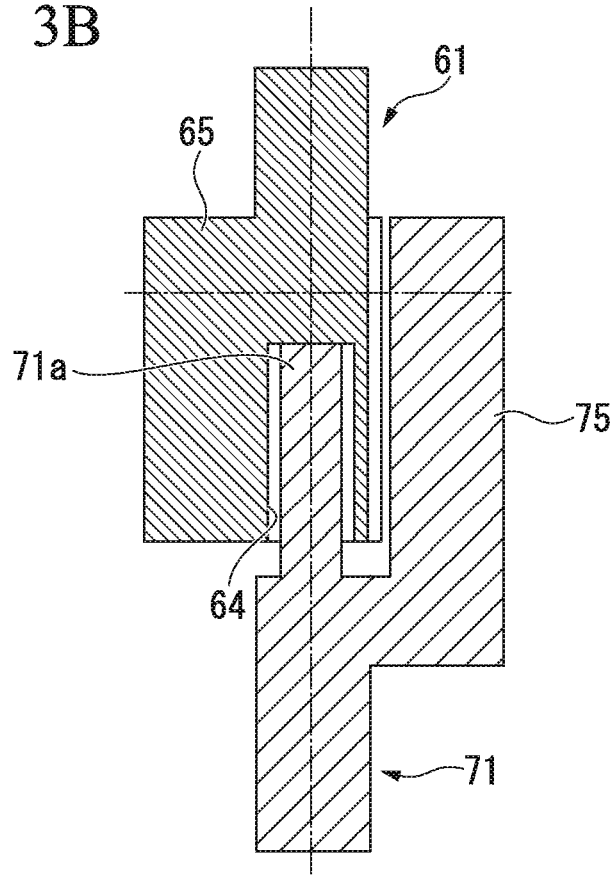
FIG. 3B is a cross-sectional view along line A-A of FIG. 3A.

FIG. 3A is a cross-sectional view of a connecting portion between the first shaft 61 and the second shaft 71 in a direction orthogonal to the axis of the first shaft 61, and FIG. 3B is a cross-sectional view along line A-A of FIG. 3A. As shown in FIGS. 3A and 3B, the end portion of the first shaft 61 is formed with a recess 64 that extends in the direction of the axis, and a fan-shaped flange 65, and the end portion of the second shaft 71 is also formed with a fan-shaped flange 75.

The first shaft 61 and the second shaft 71 are coaxially positioned by the end portion of the second shaft 71 entering the recess 64 of the first shaft 61. The respective flanges 65 and 75 are formed so as to overlap in the direction of the axis of the first shaft 61, that is, so that at least a portion thereof is located at the same height, in a state where the end portion 71a of the second shaft 71 has entered the recess 64. Additionally, the central angles of the respective flanges 65 and 75 are set to 180° or less, respectively, and gaps G as buffer regions are secured between both sides of one flange in the circumferential direction and the other.

Elastic bodies (connecting parts) 66 which are capable of an elastic deformation are arranged in the two gaps G, respectively, and the flanges 65 and 75 are connected by the two elastic bodies 66. Thereby, the first shaft 61 and the second shaft 71 are connected, and an auxiliary driving force is transmitted to the first shaft 61 from the second shaft 71. As the elastic bodies 66, well-known coil springs, rubber, or the like can be selected and used appropriately.

Moreover, the flange 75 is provided with two projections (regulating unit) 76 that protrude into the gaps G, respectively. The dimensions of the respective projections 76 are set to such a degree that the projections do not come into contact with the flange 65 in a state where compressive forces do not act on the elastic bodies 66.

The control unit 80 specifies the rotational angle (the operation amount) and rotational direction (operating direction) of the first shaft 61 on the basis of the information from the first detector 62, and calculates the magnitude and direction of an auxiliary driving force to be generated in the driving source 73 on the basis of a predetermined calculation. Moreover, the control unit 80 controls the driving source 73 to make the driving source 73 generate an auxiliary driving force and to make the second shaft 71 rotate in the same direction as the first shaft 61. This assists the rotational operation of the first shaft 61. As an example of a method of calculating the magnitude and direction of an auxiliary driving force, first, a rotational angle detected by the first detector 62, or a rotational velocity that becomes the differential value or temporal change amount of the rotational angle, and a rotational acceleration calculated from the differential value or temporal change amount are multiplied by a coefficient according to a desired assist amount. Next, the sum of some or all of the above values is obtained.

The operation of the master and slave manipulator 1 configured as described above will be described.

If the operator Op performs a manipulation input to the first arm 21, the first shaft 61 fixed to the first arm 21 rotates. The rotational angle and rotational direction of the first shaft 61 are detected by the first detector 62, and are transmitted to the control unit 80.

The control unit 80 determines the magnitude and direction of a driving force to be generated in the driving source 73 on the basis of the input from the first detector 62, and transmits an operating signal to the driving source 73. If the driving source 73 is driven, an auxiliary driving force is generated, and the second shaft 71 is rotationally driven in the same direction as the rotational direction of the first shaft 61 detected by the first detector 62. The driving force of the second shaft 71 is transmitted to the first shaft 61 through the elastic bodies 66 that connect flanges 65 and 75. Thereby, the rotational operation of the first shaft 61 is assisted, and an operational feeling of the operator Op is light. Additionally, the elastic bodies 66 mitigate the adverse effects of friction, rattling, backlash, and the like that are inherent in a driving source give to the operational feeling.

If the rotation of the first shaft 61 is stopped, the stop is transmitted to the control unit 80, and the operation of the driving source 73 is also stopped. However, since there is a slight time lag between the rotation stop of the first shaft 61 and the operation stop of the driving source 73, it is possible that during this time lag, only the second shaft 71 rotates. As only the second shaft 71 rotates, one of the two gaps G becomes small, and the flanges 65 and 75 tend to come into contact with each other. At this time, since the elastic bodies 66 arranged in the gaps G may be compressed and elastically deformed, a phenomenon in which the flanges 65 and 75 come into contact with each other and a strong impact is generated, is suppressed. However, if the elastic bodies 66 are compressed excessively, the elastic bodies may cause plastic deformation or the like beyond an elastic deformation range, and may be damaged.

In the first joint section 41 of the present embodiment, the flange 75 is provided with the projections 76 as mechanical stoppers. Thereby, since the projections 76 abut on the flange 65 if the gaps G have a predetermined size, the distance between the flange 75 and the flange 65 is reduced, and the amount of elastic deformation of the elastic bodies 66 over a predetermined amount, that is, the elastic bodies deforming excessively, is controlled. This favorably suppresses damage or the like caused by plastic deformation of the elastic bodies 66.

As described above, according to the master and slave manipulator 1 of the present embodiment to which the operating mechanism of the present embodiment is applied, the projections 76 restrict excessive deformation of the elastic bodies 66 that couple the first shaft 61 and the second shaft 71. This can provide a structure in which the elastic bodies 66 are not easily damaged, while suppressing degradation of an operational feeling by virtue of the elastic bodies 66.

In the present embodiment, the flange 75 is provided with the two projections 76. However, the flange 65 may be provided with the projections. Additionally, one of the two projections 76 may be provided on the flange 75 and the other may be provided on the flange 65.

Figure 4:
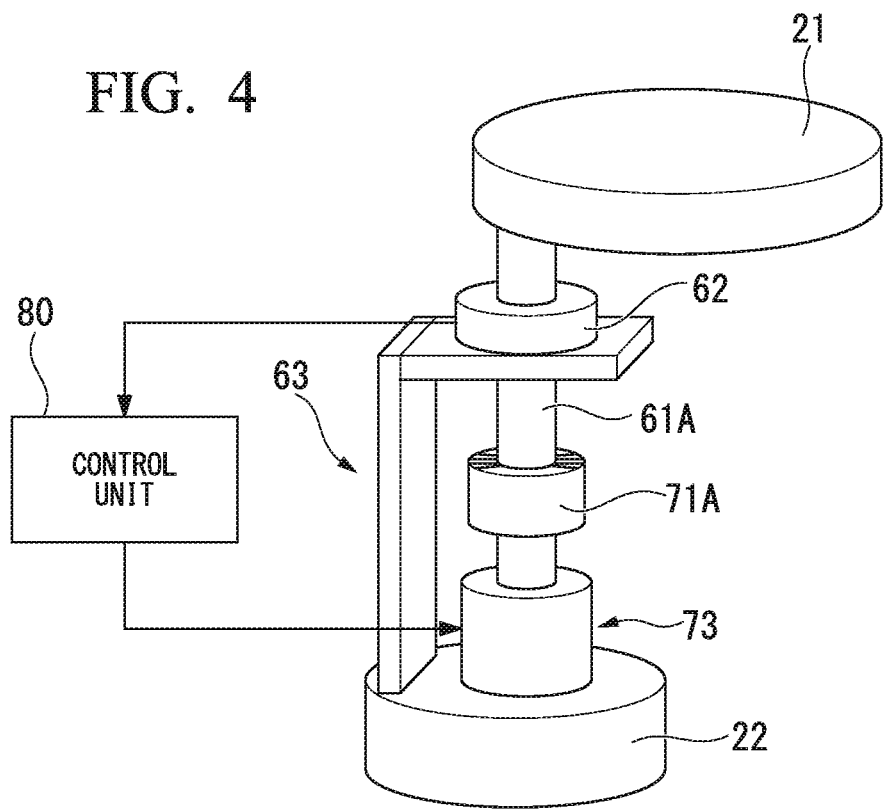
FIG. 4 is a schematic perspective view showing the structure of a first joint section in a modification of the medical manipulator of the first embodiment of the invention.
Figure 5A:
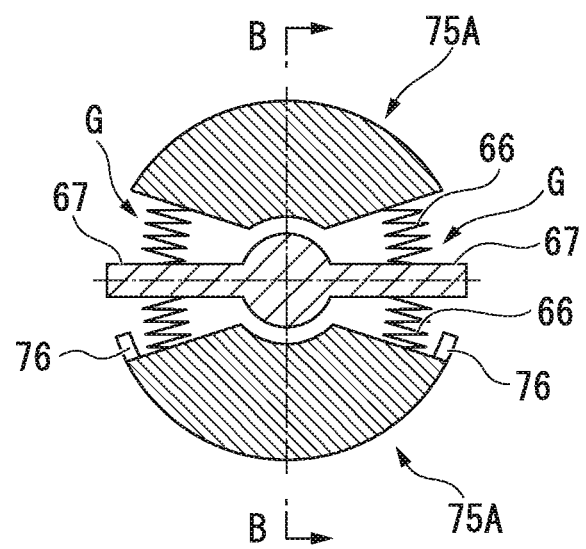
FIG. 5A is a cross-sectional view of the connecting portion between the first shaft and the second shaft of the first joint section of the medical manipulator of the first embodiment of the invention, in the direction orthogonal to the axis of the first shaft.
Figure 5B:
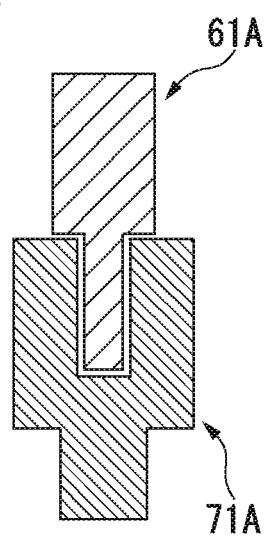
FIG. 5B is a cross-sectional view in a line B-B of FIG. 5A.

Although an example in which both the connecting portions between the first shaft and the second shaft are a substantially fan-shaped flange has been described in the present embodiment, the structure of the connecting portions is not limited to this. For example, as in a modification shown in FIGS. 4, 5A, and 5B, an end portion of one shaft (here, a second shaft 71A) may be provided with two substantially fan-shaped flanges 75A formed at a gap on both sides in the circumferential direction, an end portion of the other shaft (here, a first shaft 61A) may be provided with a pair of projection portions 67 that protrude from the outer peripheral surface, and both shafts may be coupled so that the projection portions 67 enter the gap G, respectively. In this modification, the elastic bodies 66 are arranged on both sides in a direction around the axis of each projection portion 67, and the first shaft 61A and the second shaft 71A are coupled by a total of four elastic bodies 66. That is, a structure is provided in which the first shaft 61A is pinched by the elastic bodies 66. For this reason, there is an advantage in that eccentricity resulting from a force that works between the first shaft 61A and the second shaft 71A is not easily caused, and a mechanically stable structure is provided.

Instead of providing the first shaft with the first detector that detects the operation amount, the second shaft may be provided with the detecting unit. In this case, the control unit may be configured so as to determine the magnitude and direction of an auxiliary driving force on the basis of the operation amount (second operation amount) of the second shaft that is rotated by the rotational manipulation of the first shaft.

Next, a second embodiment of the invention will be described with reference to FIGS. 6 and 7. The difference between the master and slave manipulator 101 of the present embodiment and the above-described master and slave manipulator 1 is that the regulating unit is provided in the control unit. In addition, in the following description, components common to the members already described will be designated by the same reference numerals, and duplicate description will be omitted.

Figure 6:
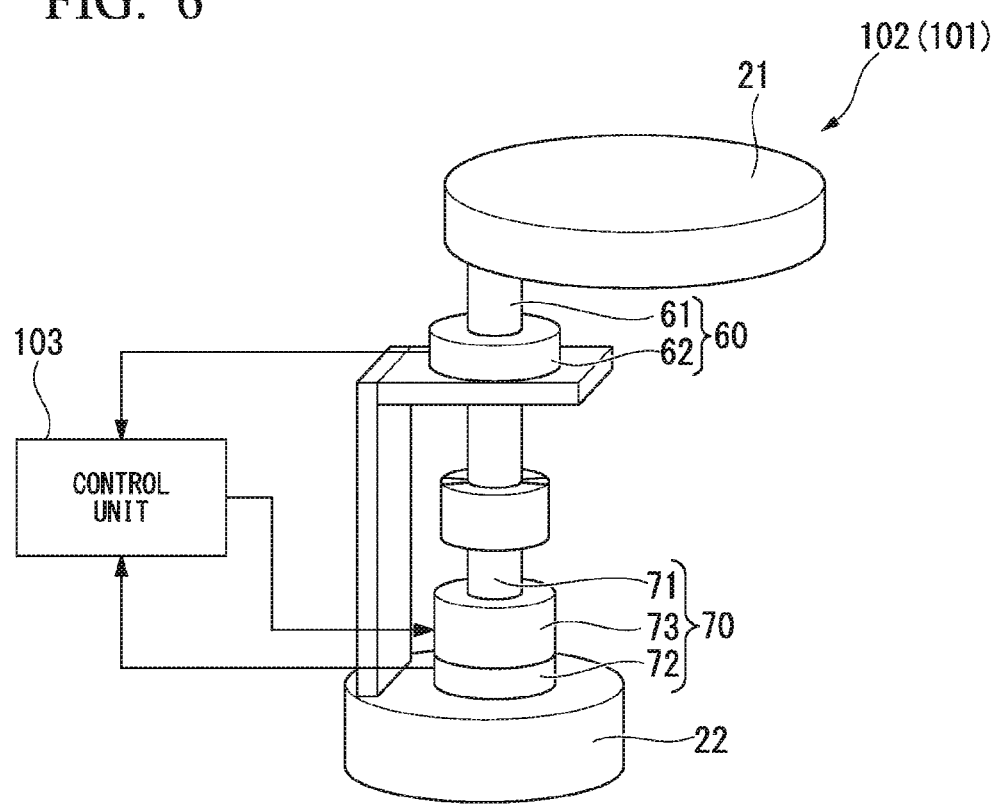
FIG. 6 is a schematic perspective view showing the structure of a first joint section of a medical manipulator to which an operating mechanism of medical device of a second embodiment of the invention is applied.
Figure 7:
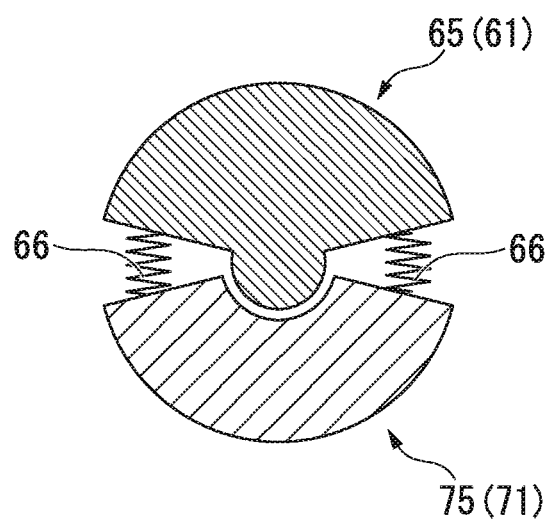
FIG. 7 is a cross-sectional view of the connecting portion between the first shaft and the second shaft of the first joint section of the medical manipulator of the second embodiment of the invention, in the direction orthogonal to the axis of the first shaft.

FIG. 6 is a schematic perspective view showing the structure of a first joint section 102 of the master and slave manipulator 101, and FIG. 7 is a cross-sectional view of a connecting portion between the first shaft 61 and the second shaft 71 in the first joint section 102 in the direction orthogonal to the axis of the first shaft 61. The height of the cross-section is equal to that of FIG. 3A.

As shown in FIG. 6, a second detector 72 that detects the operation amount of the second shaft 71 is attached to the second shaft 71. As the second detector 72, the same rotary encoder or the like as the first detector 62 can be used.

As shown in FIG. 7, the first shaft 61 and the second shaft 71 include the same flanges 65 and 75 as the first embodiment, respectively, but the projections 76 are not provided. Instead of this, as a control unit 103 controls the operation of the driving source 73 in a predetermined aspect, the deformation of the elastic bodies 66 is restricted so as not to deform excessively. Detailed description will be made below.

First, the control unit 103 determines the magnitude and direction of a driving force to be generated in the driving source 73 on the basis of the input from the first detector 62, and transmits an operating signal to the driving source 73. This point is almost the same as that of the first embodiment.

If the second shaft 71 rotates, the operation amount of the second shaft 71 is detected by the second detector 72, and transmitted to the control unit 103. After transmission from the second detector 72 has started, the control unit 103 calculates a difference $\Delta\theta$ between a rotational angle $\theta_1$ of the first shaft 61 sent from the first detector 62 and a rotational angle $\theta_2$ of the second shaft 71 sent from the second detector 72, and determines the direction and magnitude of the amount $i_m$ of operation of the driving source 73 on the basis of $\Delta\theta$.

The control unit 103 determines whether or not an operating signal is transmitted on the basis of whether or not the absolute value of $\Delta\theta$ is less than a predetermined value $\theta_d$, before the operating signal is transmitted to the driving source 73. If this determination is "Yes", the control unit 103 transmits an operating signal to the driving source 73. On the other hand, if this determination is "No", that is, if the expression $-\theta_d < \Delta\theta < \theta_d$ is no longer satisfied, the control unit 103 updates the amount $i_m$ of operation to zero because the flange 65 and the flange 75 are too close and the elastic bodies 66 may be excessively deformed. Accordingly, the driving source 73 that has received the operating signal is stopped, and the rotation of the second shaft 71 by the driving source 73 is no longer performed. For this reason, the detection resolution powers of the first detector 62 and the second detector 72 are set to be smaller than $\theta_d$, and the first detector 62 and the second detector 72 have enough resolving power to manipulate an ordinary master and slave manipulator.

In the master and slave manipulator 101 of the present embodiment, the control unit 103 updates the operation amount of the driving source 73 to zero if the value of $\Delta\theta$ that is the difference between the operation amount of the first shaft 61 and the operation amount of the second shaft 71 deviates from a predetermined range. That is, the control unit 103 functions as a determination unit and regulating unit that determines whether or not the regulating unit is made to operate, whereby the difference between the operation amount of the first shaft 61 and the operation amount of the second shaft 71 is limited to less than a predetermined value, preventing excessive deformation of the elastic bodies 66.

Accordingly, similar to the first embodiment, a structure can be provided in which the elastic bodies are not easily damaged, while suppressing degradation of an operational feeling by the elastic bodies.

Since it is not necessary to provide mechanical stoppers, such as the projections 76, the structure of the connecting portion between the first shaft 61 and the second shaft 71 can be simplified.

Next, a third embodiment of the invention will be described with reference to FIGS. 8 and 9. The difference between the master and slave manipulator 111 of the present embodiment and the master and slave manipulator of the above-described respective embodiments is that a switching unit that switches between an on-state and an off-state of transmission of a driving force from the driving source to the second shaft is included.

Figure 8:
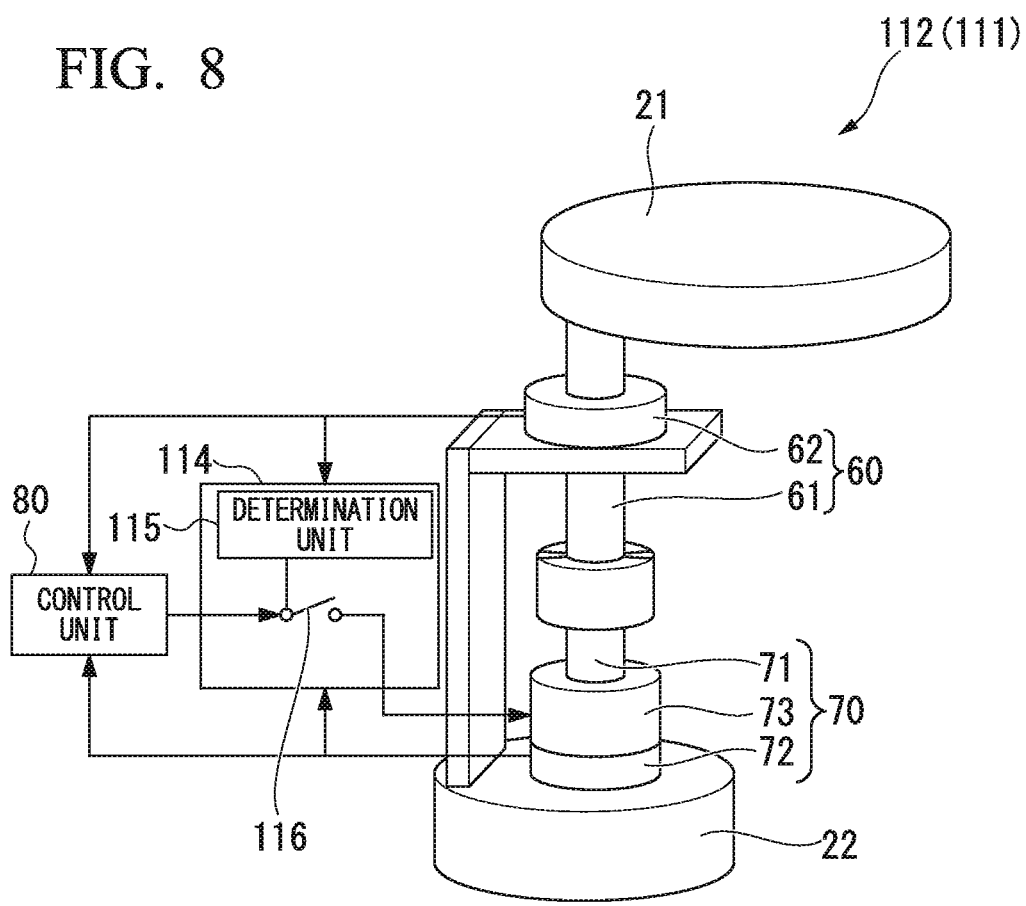
FIG. 8 is a schematic perspective view showing the structure of a first joint section of a medical manipulator to which an operating mechanism of medical device of a third embodiment of the invention is applied.

FIG. 8 is a schematic perspective view showing the structure of a first joint section 112 of a master and slave manipulator 111. The structure of the connecting portion between the first shaft 61 and the second shaft 71 is the same as that of the second embodiment. A switching unit (regulating unit) 114 is provided between the control unit 80 and the driving source 73. The switching unit 114 includes a determination unit 115 that determines the difference between the operation amount of the first shaft 61 and the operation amount of the second shaft 71, and a switch 116 that is turned on and off by the determination unit 115.

The determination unit 115 has an arithmetic circuit or an arithmetic program, and is connected to the first detector 62 and the second detector 72. The determination unit 115 has almost the same aspect as the control unit 103 of the second embodiment, and determines whether or not the absolute value of the difference AB between the operation amount of the first shaft 61 and the operation amount of the second shaft 71 is less than the predetermined value $\theta_d$.

The switch 116 is a well-known electric switch, and is manipulated to switch between an on-state and an off-state of operating signal transmission to the driving source 73 from the control unit 80.

The operation of the master and slave manipulator 111 configured as described above will be described. Similar to the first embodiment, the control unit 80 generates an operating signal for the driving source 73 according to the input from the first detector 62, and continues transmission toward the driving source 73.

In parallel with this, in the switching unit 114, the determination unit 115 repeatedly determines whether or not the absolute value of AB is less than a predetermined value $\theta_d$ at predetermined intervals. If this determination is "Yes", the limitation by the regulating unit is determined to be unnecessary, and the ON state of the switch 116 is maintained. On the other hand, if this determination is "No", the limitation by the regulating unit is determined to be necessary, the switch 116 is manipulated by the determination unit 115 so as to bring about an OFF state, and the operating signal transmission to the driving source 73 from the control unit 80 is interrupted. As a result, the driving source 73 stops.

In the master and slave manipulator 111 of the present embodiment, transmission of an operating signal from the control unit 80 to the driving source 73 is interrupted by the switching unit 114 if the value of $\Delta\theta$ that is the difference between the operation amount of the first shaft 61 and the operation amount of the second shaft 71 deviates from a predetermined range. This limits the difference between the operation amount of the first shaft 61 and the operation amount of the second shaft 71 to less than a predetermined amount, preventing excessive deformation of the elastic bodies 66.

Accordingly, similar to the first embodiment, a structure can be provided in which the elastic bodies are not easily damaged, while suppressing degradation of an operational feeling by virtue of the elastic bodies.

Although the example in which an on-state and an off-state of transmission of a driving force to the second shaft 71 from the driving source 73 is electrically switched using the switch 116 has been described in the present embodiment, the switching aspect of the switching unit is not limited to this.

Figure 9:
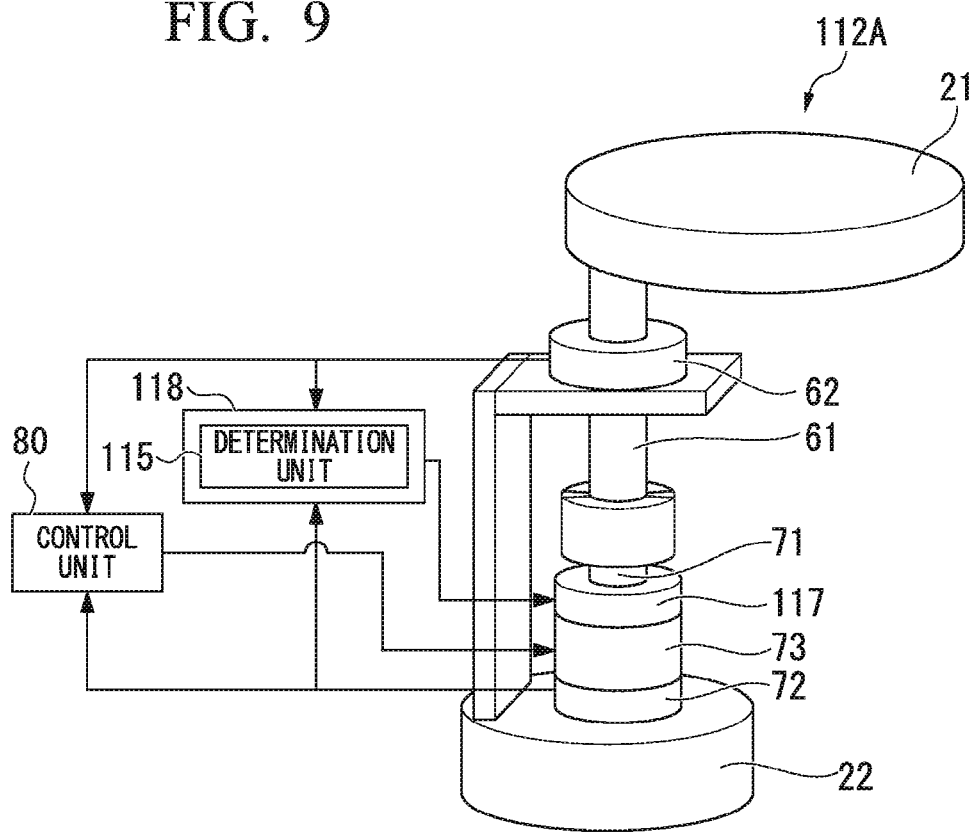
FIG. 9 is a schematic perspective view showing the structure of a first joint section in a modification of the medical manipulator of the third embodiment of the invention.

FIG. 9 is a view showing a first joint section 112A in a modification of the present embodiment. A clutch 117 is attached to the driving source 73, and the driving force of the driving source 73 is transmitted to the second shaft 71 via the clutch 117. A switching unit 118 is not connected to the control unit 80. Moreover, the switching unit 118 does not include a switch 116, and is connected to the clutch 117.

In the first joint section 112A, if the above determination in the determination unit 115 is "No", the clutch 117 is manipulated by the determination unit 115 so as to bring about an OFF state, and transmission of a driving force to the second shaft 71 from the driving source 73 is mechanically interrupted. Although this is an example, an on-state and an off-state of transmission of a driving force from the driving source to the second shaft may be mechanically switched in this way.

In the present embodiment, in all cases including the modification, the switching unit is provided separately from the control unit. Therefore, for example, in a case where the control unit has caused a malfunction, damage or the like caused by deformation of the elastic bodies can also be reliably prevented.

A fourth embodiment of the invention will be described with reference to FIGS. 10A, 10B, 11A, and 11B. The difference between the master and slave manipulator 121 of the present embodiment and the master and slave manipulator of the above-described respective embodiments is that braking unit that brakes the operation of the second shaft is included.

Figure 10A:
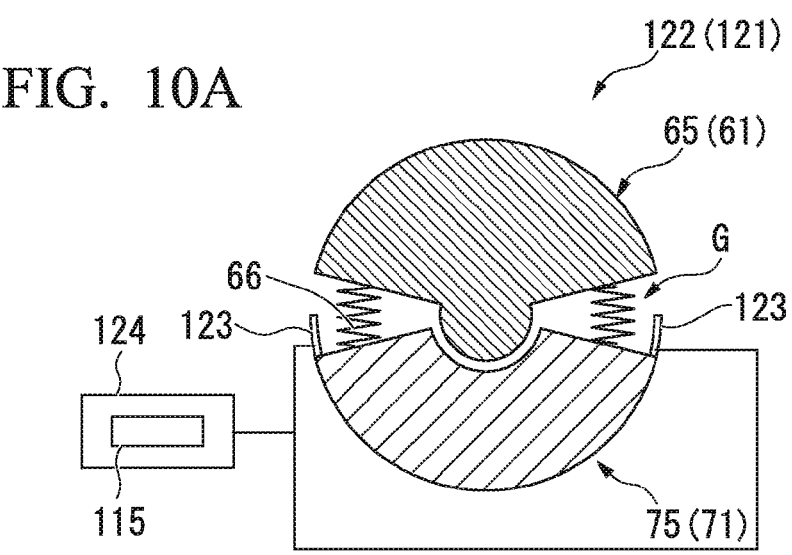
FIG. 10A is a cross-sectional view of the connecting portion between the first shaft and the second shaft of a first joint section in a medical manipulator to which an operating mechanism of medical device of a fourth embodiment of the invention is applied, in the direction orthogonal to the axis of the first shaft.
Figure 10B:
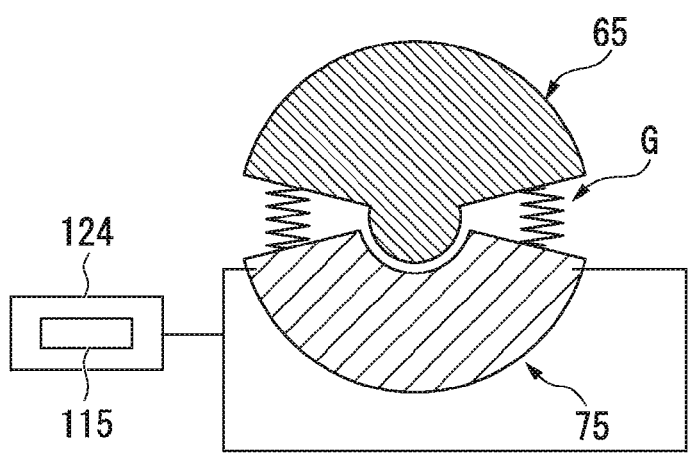
FIG. 10B is a cross-sectional view of the connecting portion between the first shaft and the second shaft of the first joint section in the medical manipulator to which the operating mechanism of medical device of the fourth embodiment of the invention is applied, in the direction orthogonal to the axis of the first shaft.

FIGS. 10A and 10B are cross-sectional views showing the connecting portion between the first shaft 61 and the second shaft 71 in a first joint section 122 of a master and slave manipulator 121. The flange 75 of the second shaft 71 is provided with braking projections (braking unit) 123 that protrude into the gaps G between the flange 75 and the flange 65.

The braking projections 123 includes, for example solenoids or the like, and can be made to protrude into the gaps G or to be accommodated within the flange 75 as shown in FIG. 10B, by an electrical signal. The braking projections 123 are connected to a switching unit 124. The configuration of the switching unit 124 is the same as that of the switching unit 118, and includes only the determination unit 115. The clutch is not attached to the driving source 73.

In the master and slave manipulator 121 of the present embodiment, if the above determination in the determination unit 115 is "No", the braking projections 123 are manipulated by the determination unit 115, and protrude into the gaps G The braking projections 123 brake so as to roll the flange 65 of the first shaft 61 back using a protruding operation. After the braking projections 123 have protruded to a predetermined length, the projections abut on the flange 65, suppressing excessive deformation of the elastic bodies 66 similar to the first embodiment. Accordingly, similar to the first embodiment, a structure can be provided in which the elastic bodies are not easily damaged, while suppressing degradation of an operational feeling by virtue of the elastic bodies.

Additionally, since the braking projections 123 that are regulating unit works so as to brake the rotational driving of the first shaft 61 in an early stage, the rotational velocity of the first shaft 61 can be slightly reduced before the flange 65 and the braking projections 123 butt against each other strongly. Therefore, transmission of a strong impact to the load side can be more reliably suppressed.

Figure 11A:
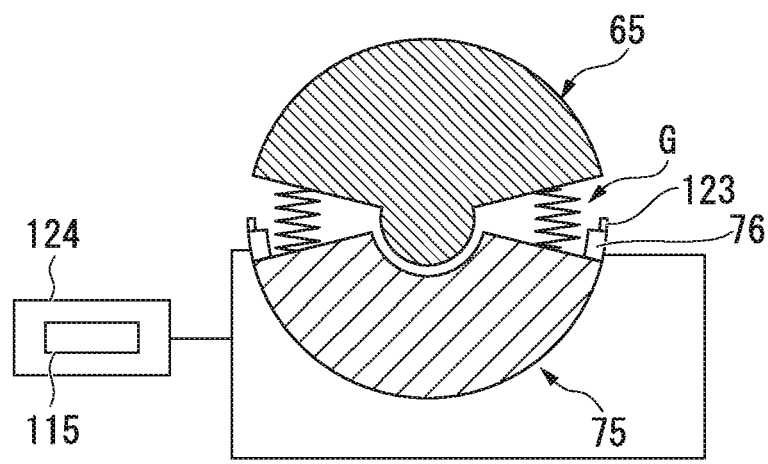
FIG. 11A is a cross-sectional view of the connecting portion between the first shaft and the second shaft of a first joint section in a modification of the medical manipulator of the fourth embodiment of the invention, in the direction orthogonal to the axis of the first shaft.
Figure 11B:
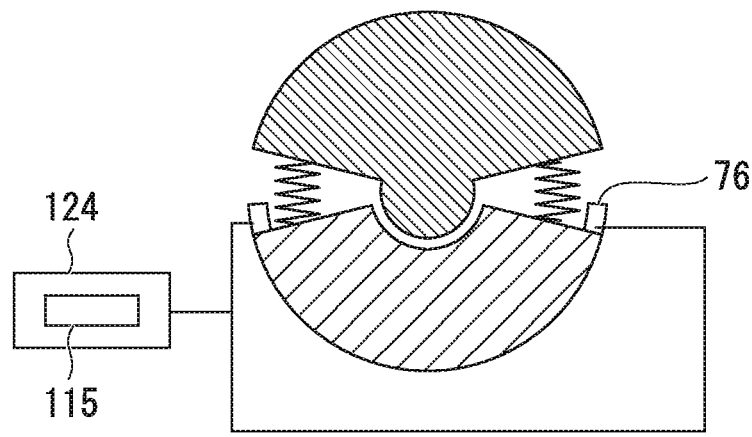
FIG. 11B is a cross-sectional view of the connecting portion between the first shaft and the second shaft of the first joint section in a modification of the medical manipulator of the fourth embodiment of the invention, in the direction orthogonal to the axis of the first shaft.

Although an example in which the braking projections protrude or withdraw from the flange has been described in the present embodiment, instead of this, as shown in FIGS. 11A and 11B, braking projections 123 may be configured so as to protrude and retract from the projections 76 as the regulating unit provided on the flange 75. In this configuration, by appropriately setting the operation aspect of the determination unit, a braking range where a braking force is generated can be changed or the protruding length of the projections 76 as rigid projections (that is, functions as physical stoppers) can be changed. This can variously set the braking of the second shaft 71 or the aspect of deformation suppression of the elastic bodies. As a result, even if the elastic bodies are changed to aspects with different elastic modulus according to the use environment of the manipulator, tissues to be treated, or the like, it is possible to perform suitable control according to the elastic bodies after the change.

The braking projections may be provided on the first shaft side. In this case, transmission of a strong impact to the load side can be more effectively suppressed by braking the second shaft driven by the driving source.

Moreover, one of the two braking projections may be provided on the second shaft, and the other projection may be provided on the first shaft.

Figure 12:
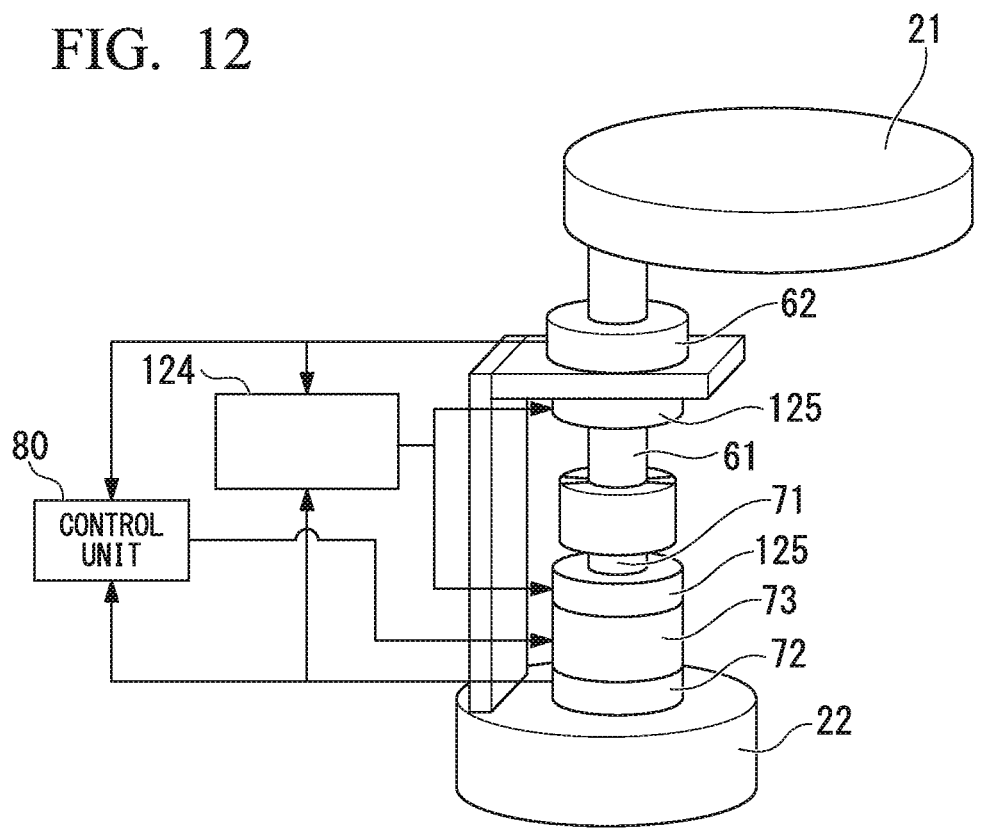
FIG. 12 is a schematic perspective view showing the structure of a fourth joint section in another modification of the medical manipulator of the fourth embodiment of the invention.

Additionally, as in the modification shown in FIG. 12, brakes 125 as braking unit may be attached to the first shaft 61 and the second shaft 71. As the brakes 125, those having various well-known mechanisms, such as a mechanical friction type and a fluid resistance type, can be appropriately selected and adopted.

Although the respective embodiments of the invention have been described above, the technical scope of the invention is not limited to the above embodiments, and without departing from the scope of the invention, various changes or omissions can be made to respective constituent elements or omissions, or constituents of the respective embodiments can be combined.

Figure 13:
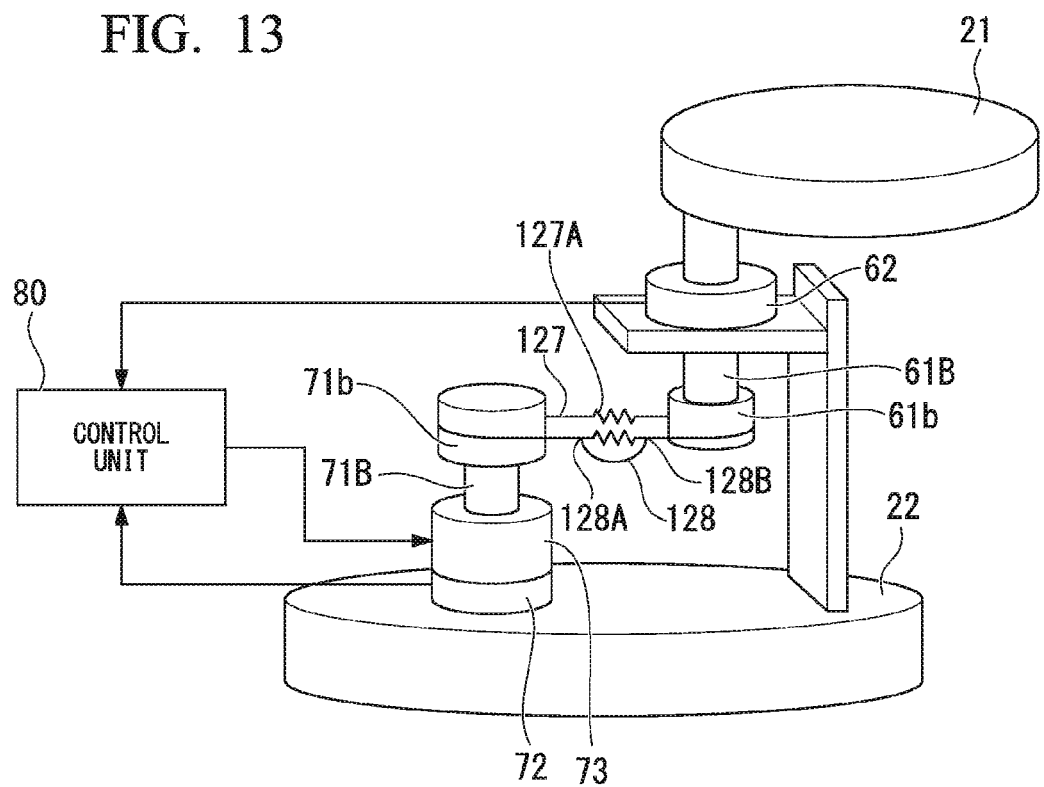
FIG. 13 is a schematic perspective view showing the structure of a first joint section in a medical manipulator related to a modification of the embodiment of the invention.

For example, as in a modification shown in FIG. 13, a first shaft 61B and a second shaft 71B do not need to be coaxially connected. In this modification, end portions of the first shaft 61B and the second shaft 71B are formed in a disk shape, respectively, and function as pulleys 61b and 71b. A transmission member (connecting part) 127 having an elastic deformation region 127A, such as a wire or a belt, is hung around on the pulleys 61b and 71b, and the first shaft 61B and the second shaft 71B are connected so as to be able to transmit an auxiliary driving force.

Respective end portions 128A and 128B of the limiting wire 128 are attached to the transmission members 127 on both sides of the elastic deformation region 127A. The limiting wire 128 has rigidity of a predetermined value or more, and is longer than the distance between connection points on the transmission member 127 where the end portions 128A and 128B are connected in a state where the elastic deformation region 127A does not deform. For this reason, the limiting wire 128 is loose in a state where the elastic deformation region 127A does not deform. Accordingly, the limiting wire 128 permits that the elastic deformation region 127A can be stretched until the region becomes linear, but restricts deformation of the elastic deformation region 127A, suppressing plastic deformation, occurrence of damage, or the like after the region becomes linear. If the elastic deformation region 127A is compressed to a predetermined length, further deformation of the elastic deformation region 127A by its own rigidity is suppressed. This suppresses excessive deformation of the elastic deformation region 127A that functions as an elastic body.

Here, although an example in which the limiting wire 128 that functions as a mechanical stopper is included as the regulating unit has been described, as in the above-described second embodiment, it is needless to say that combination with electrical regulating unit may be made.

Figure 14:
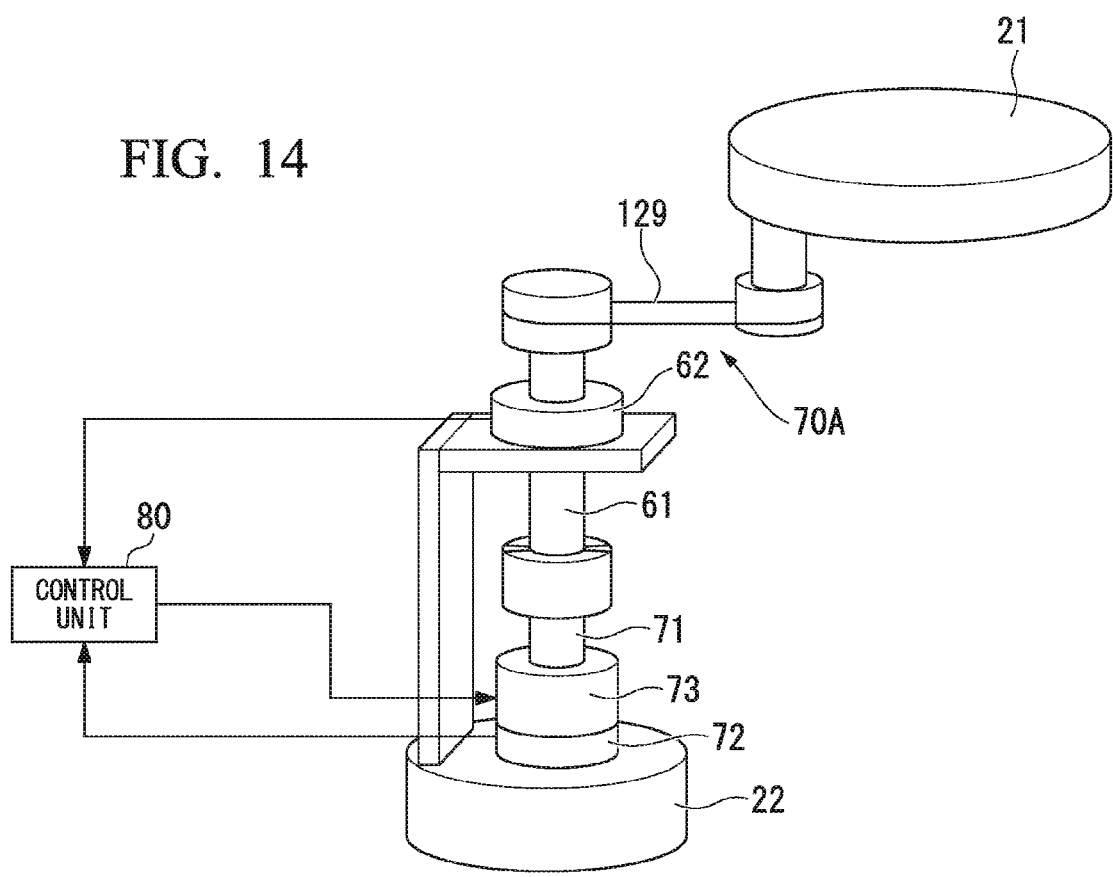
FIG. 14 is a schematic perspective view showing the structure of a first joint section in a medical manipulator related to another modification of the embodiment of the invention.

The mechanism in which the transmission member is hung around to transmit rotation may be provided at a first shaft part 70A on the load side as in a modification shown in FIG. 14 in addition to the connecting portion between the first shaft and the second shaft. Here, a region around which the transmission member 129 is hung can also be a connecting portion between the first shaft and a load (the first arm 21), or can also be a connecting portion of two split shafts of the first shaft.

Moreover, it is needless to say that such a transmission mechanism may be provided at the second shaft part on the opposite side.

Although an example in which the first shaft and the second shaft operate to rotate around an axis has been described in the respective above-described embodiments, the operation aspect of the first shaft and the second shaft is not limited to this.

Figure 15:
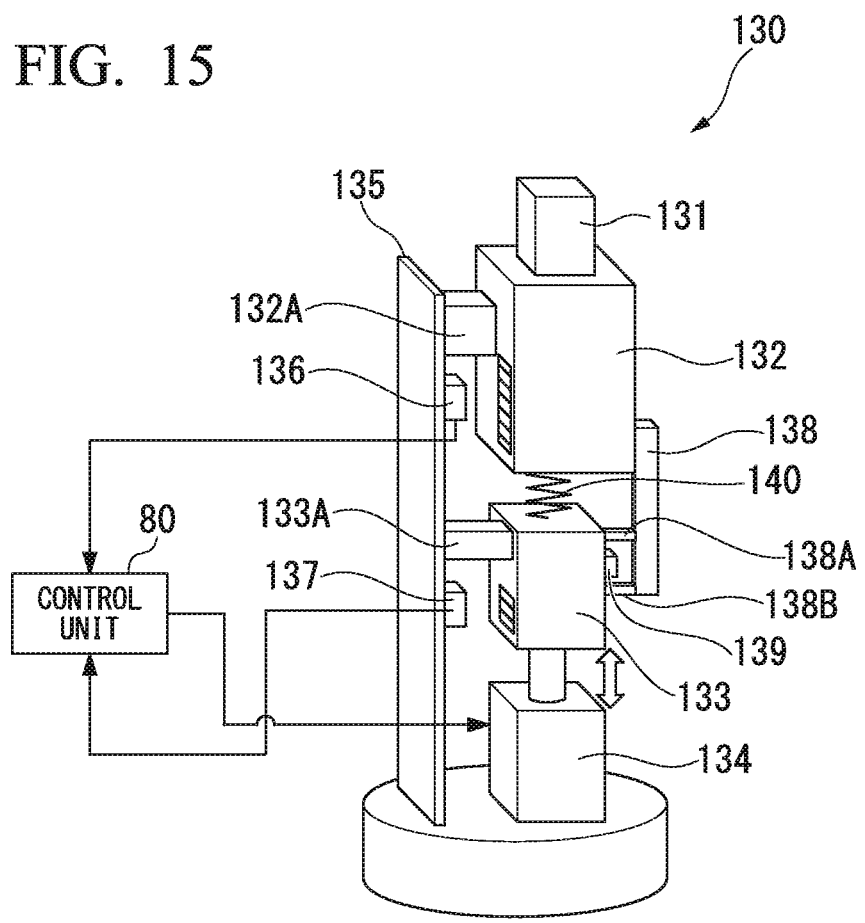
FIG. 15 is a schematic perspective view showing the structure of a first joint section in a medical manipulator related to another modification of the embodiment of the invention.

A modification shown in FIG. 15 shows a joint section (operating mechanism) 130 in the master and slave manipulator related to the modification of the embodiment of the invention. In the joint section 130, a first shaft 132 and a second shaft 133 linearly move in a longitudinal direction by moving the first arm 131 in the longitudinal direction. The second shaft 133 is driven by a driving source 134 including, for example, a linear actuator or the like, and the manipulation of the first arm 131 is assisted by transmitting a driving force to the first shaft 132 through an elastic body 140.

Figure 16:
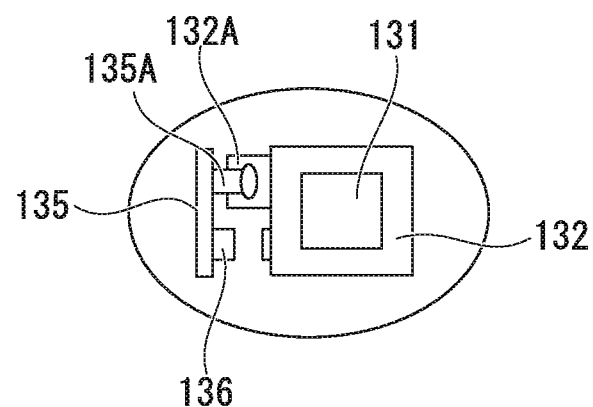
FIG. 16 is a plan view of a medical manipulator related to another modification of the embodiment of the invention.

FIG. 16 is a plan view when the joint section 130 is seen from the first arm 131 side. As shown in FIGS. 15 and 16, a slide 132A provided at the first shaft 132 and a slide 133A provided at the second shaft 133 are respectively engaged with rails 135A and 135B (not shown) fixed to a support 135. Through this configuration, the first shaft 132 and the second shaft 133 linearly moves parallel (including substantially parallel) to the support 135 with the rails 135A and 135B as guides.

Although a first detector 136 and a second detector 137 are of a reflective linear encoder using carrier luminescence, respectively, this is an example. The first and second detectors are not particularly limited if the detection of the amounts of linear movement operation of the first shaft 132 and the second shaft 133 can be detected.

Regulating unit 138 is attached to the external surface of the first shaft 132, and extends toward the second shaft 133. A pair of projections 138A and 138B is provided at a distance from each other at the end portion of the regulating unit 138 on the side of the second shaft 133. The projections 138A and 138B are located so as to pinch a limiting projection 139 that protrudes from the external surface of the second shaft 133, in the linear movement direction of the first shaft 132. If the distance between the first shaft 132 and the second shaft 133 is out of a predetermined range, either of the projections 138A and 138B and the limiting projection 139 interfere with each other. This holds the distance between the first shaft 132 and the second shaft 133 within a fixed range, suppressing excessive deformation of the elastic body 140.

As such, the operating mechanism related to the embodiment of the invention can also be applied to a case where the first shaft and the second shaft are linearly moved. Of course, even in this modification, electrical regulating unit may be used instead of mechanical regulating unit like the regulating unit 138.

Figure 17:
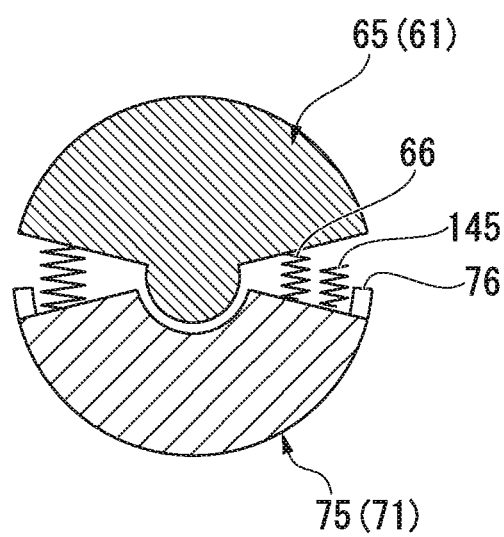
FIG. 17 is a cross-sectional view of the connecting portion between the first shaft and the second shaft of a first joint section in a medical manipulator related to another modification of the embodiment of the invention, in the direction orthogonal to the axis of the first shaft.

Moreover, as in a modification shown in FIG. 17, a limiting elastic body 145 that come into contact with the flange 65 earlier than the projections 76 may be independently arranged, separately from the elastic bodies 66 that connect the first shaft 61 and the second shaft 71. Then, the elastic bodies 66 are compressed first, and the elastic bodies 66 and the limiting elastic body 145 are compressed after that. For this reason, when the elastic bodies 66 and the limiting elastic body 145 are compressed, since the elastic modulus thereof is different from that when only the elastic bodies 66 are compressed, a reaction force to be transmitted from the first shaft 61 to a load also changes and an operational feeling changes. As a result, the operator can recognize that the magnitude of a manipulation input applied to the load or the like is falling with an improper range, and can urge the operator to make a proper correction, such as making the manipulation input small, thereby further improving operability.

In the modification shown in FIG. 17, the limiting elastic body 145 is provided only at the right of the flange 75 in the drawing. However, the limiting elastic body may be provided on the left in the drawing, and may be provided on the flange 65 side.

Figure 19A:
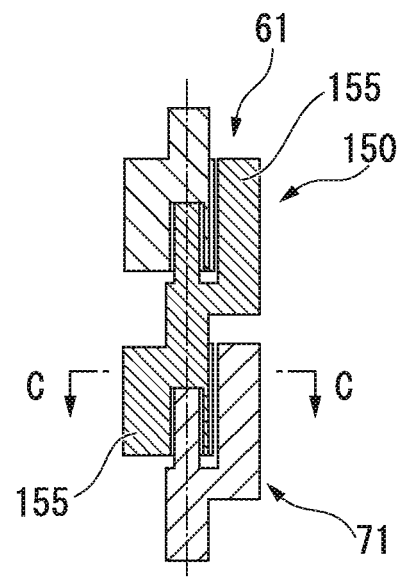
FIG. 19A is a cross-sectional view of the connecting portion between the first shaft and the second shaft of a first joint section of a medical manipulator of another modification of the embodiment of the invention, in the direction of the axis of the first shaft.
Figure 19B:
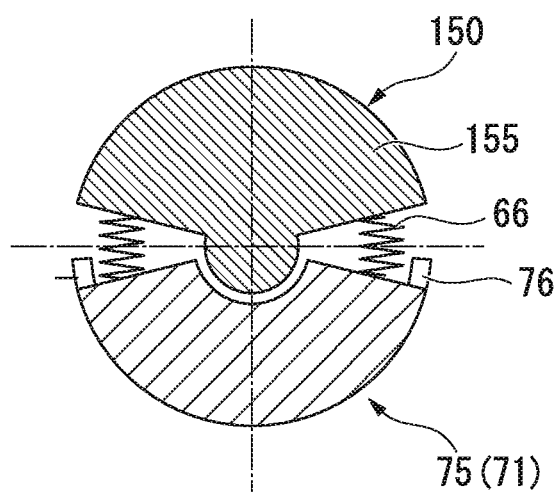
FIG. 19B is a cross-sectional view along line C-C of FIG. 19A.

Moreover, as shown in FIGS. 18 and 19, the first shaft 61 and the second shaft 71 may be connected through an intermediate shaft 150 having substantially fan-shaped flanges 155 on both ends in the direction of the axis. In this case, as shown in FIGS. 19A and 19B, the first shaft 61 and the intermediate shaft 150 are connected by the elastic bodies 66, and the intermediate shaft 150 and the second shaft 71 are connected by the elastic bodies 66. In such a structure, elastic bodies having different elastic moduli can be used on the first shaft side and on the second shaft side. Therefore, it is also possible to select most suitable elastic bodies in consideration of the quality of materials of the respective shafts. At this time, the regulating unit, such as the projections 76, may be provided in a plurality of places. In the case of the mechanical regulating unit, the projections may be provided at any of the first shaft 61, the second shaft 71, and the intermediate shaft 150.

In addition, in this modification, as described above, the first shaft and the second shaft can be connected through the intermediate shaft. Otherwise, the first shaft and the second shaft can be connected by the elastic bodies, without through the intermediate shaft, and the first shaft or the second shaft may have an elastic connecting part therein.

In the master and slave manipulator related to the embodiment of the invention, a joint section that has such an operating mechanism may be provided on the slave arm side. In the case of the slave arm, usually, a load-side manipulation input is also performed by the driving source. Therefore, the effect of improvement in an operational feeling is not easily obtained except for, for example, a case where the operator directly controls the slave arm temporarily. However, since excessive backlash or the like of an assist driving source serves as a cause of damage to the joint section itself, there is a merit that the slave arm in which the joint section is not easily damaged can be configured.

Additionally, the joint section having the operating mechanism related to the embodiment of the invention can be applied to apparatuses with an arm or an operating mechanism holding a treatment tool, an endoscope, other medical instruments, in addition to the master and slave manipulator.

While preferred embodiments of the present invention have been described, the present invention is not limited to the embodiments.
Additions, omissions, substitutions, and other variations may be made to the present invention without departing from the spirit and scope of the present invention. The present invention is not limited by the above description, but by the appended claims.

The invention claimed is:

1. An operating mechanism of a medical device, the operating mechanism comprising:
    a first motion transmission part fixed to a load-side member, the load side member being provided to directly receive an operation input from an operator;
    a driving source configured to generate an auxiliary driving force that assists an operation of the first motion transmission part;
    a second motion transmission part configured to be operated by the auxiliary driving force;
    a connecting part which connects the first motion transmission part with the second motion transmission part, transmits the auxiliary driving force from the second motion transmission part to the first motion transmission part, wherein at least a part of the connecting part is capable of an elastic deformation;
    a detecting unit configured to detect at least one of a first operation amount of the first motion transmission part and a second operation amount of the second motion transmission part;
    a control unit that configured to control the driving source based on the first operation amount and the second operation amount detected by the detecting unit; and
    a regulating unit configured to regulate so that an amount of the elastic deformation of the connecting part is equal to or more than a predetermined amount.

2. The operating mechanism of medical device according to claim 1,
    wherein the regulating unit is configured to limit a difference between the first operation amount of the first motion transmission part and the second operation amount of the second motion transmission part to less than a predetermined amount.

3. The operating mechanism of medical device according to claim 2,
    wherein the regulating unit is a mechanical stopper provided in a connecting portion between the first motion transmission part and the second motion transmission part.

4. The operating mechanism of medical device according to claim 3,
    wherein the stopper includes a braking unit configured to brake at least one of the first motion transmission part and the second motion transmission part.

5. The operating mechanism of medical device according to claim 2,
    wherein the detecting unit has a first detector that detects the first operation amount of the first motion transmission part and a second detector that detects the second operation amount of the second motion transmission part, and
    wherein the regulating unit is configured to limit the difference to less than a predetermined amount based on the detection values of the first detector and the second detector.

6. The operating mechanism of medical device according to claim 5, further comprising a determination unit that determines whether or not the regulating unit is made to operate based on the detection values of the first detector and the second detector.

7. The operating mechanism of medical device according to claim 6,
    wherein the regulating unit switches between an on-state and an off-state of transmission of the auxiliary driving force to the second motion transmission part from the driving source based on the determination of the determination unit.

8. The operating mechanism of medical device according to claim 6,
wherein the regulating unit includes a braking unit configured to brake at least one of the first motion transmission part and the second motion transmission part based on the determination of the determination unit.

9. The operating mechanism of medical device according to claim 6,
wherein the control unit controls the operation of the driving source based on the determination of the determination unit, and functions as the regulating unit.

10. The operating mechanism of medical device according to claim 6,
wherein the regulating unit switches between an on-state and an off-state of transmission of an operating signal to the driving source from the control unit based on the determination of the determination unit.

11. A medical manipulator comprising:
an operating mechanism of a medical device, the operating mechanism comprising:
a first motion transmission part fixed to a load-side member, the load side member being provided to directly receive an operation input from an operator;
a driving source configured to generate an auxiliary driving force that assists an operation of the first motion transmission part;
a second motion transmission part configured to be operated by the auxiliary driving force;
a connecting part which connects the first motion transmission part with the second motion transmission part, transmits the auxiliary driving force from the second motion transmission part to the first motion transmission part, wherein at least a part of the connecting part is capable of an elastic deformation;
a detecting unit configured to detect at least one of a first operation amount of the first motion transmission part and a second operation amount of the second motion transmission part;
a control unit that configured to control the driving source based on the first operation amount and the second operation amount detected by the detecting unit; and
a regulating unit configured to regulate so that an amount of the elastic deformation of the connecting part is equal to or more than a predetermined amount.

* * * * *